United States Patent [19]

Ohsawa et al.

[11] Patent Number: 5,079,232
[45] Date of Patent: Jan. 7, 1992

[54] COMPOUND KS-505 USEFUL FOR IMPROVING CEREBRAL FUNCTION

[75] Inventors: Keiko Ohsawa; Satoshi Nakanishi, Both of Tokyo, Japan; Hiroshi Kase, Merseyside, United Kingdom; Isao Kawamoto, Kanagawa; Tohru Yasuzawa, Osaka; Yutaka Saito; Hiroshi Sano, both of Tokyo; Shizuo Shiozaki; Katsuichi Shutoh, both of Shizuoka, all of Japan

[73] Assignee: Kyowa Hakko Rogyo Kabushiki Kaisha, Japan

[21] Appl. No.: 447,891

[22] Filed: Dec. 8, 1989

[30] Foreign Application Priority Data

Dec. 9, 1988 [JP] Japan .................. 63-311441

[51] Int. Cl.$^5$ .................. A61K 31/71; C07H 15/24
[52] U.S. Cl. .................. 514/25; 536/4.4; 536/16.8; 536/18.1
[58] Field of Search .................. 536/16.8, 18.1, 4.4; 514/25

[56] References Cited

U.S. PATENT DOCUMENTS 4,879,376  11/1989  Foresta et al. .................. 536/18.1

FOREIGN PATENT DOCUMENTS 3040246  5/1980  Fed. Rep. of Germany .

OTHER PUBLICATIONS

Oshima et al., Chemical Abstracts, vol. 101, No. 20, Nov. 12, 1984, No. 117236r, p. 376.
Omura et al., Chemical Abstracts, vol. 108, No. 15, Apr. 11, 1988, No. 130054e, p. 601.

*Primary Examiner*—Johnnie R. Brown
*Assistant Examiner*—Elli Peselev
*Attorney, Agent, or Firm*—Schweitzer Cornman & Gross

[57] ABSTRACT

A new compound designated KS-505 having amnesia-inhibiting activity may be prepared by fermentation of a suitable strain of *Streptomyces*, preferably *Streptomyces argenteolus* A-2 (FERM BP-2065). The compound is thought to have the structure:

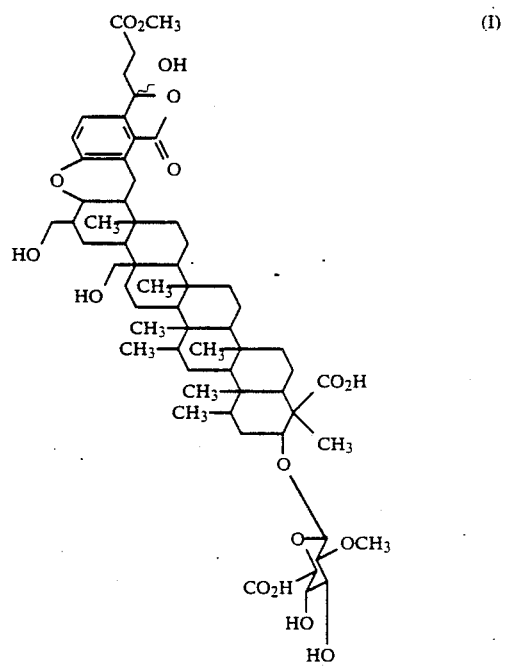

6 Claims, No Drawings

COMPOUND KS-505 USEFUL FOR IMPROVING CEREBRAL FUNCTION

The present invention relates to a new compound originating from a microorganism and having physiological pharmaceutically acceptable salts thereof, processes for their preparation and pharmaceutical compositions containing the same.

It was previously well known that, for example, various microorganisms of the genus Streptomyces are capable of producing physiologically active substances. However, any substance originating from microorganisms of the genus Streptomyces and capable of improving the cerebral function had not previously been reported.

We have now unexpectedly found that a new compound of microbial origin is capable of improving the cerebral function.

Therefore, the present invention provides a new compound capable of improving the cerebral function, pharmaceutically acceptable salts thereof, processes for their preparation and pharmaceutical compositions containing the same.

According to one aspect of the present invention, there is provided a compound (hereinafter referred to as KS-505) represented by the following formula (I):

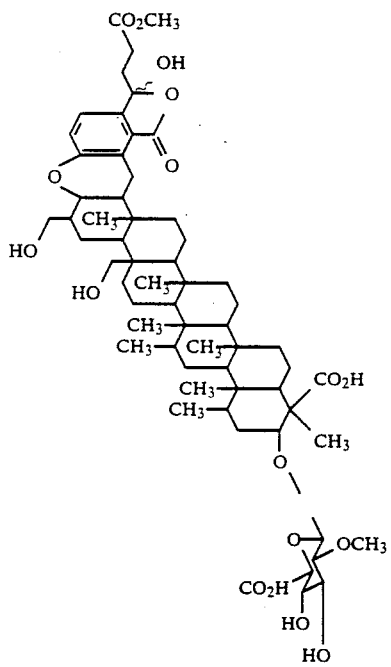

(I)

and pharmaceutically acceptable salts thereof.

KS-505 according to the present invention is capable of improving the cerebral function and may be used, for example, for curing and preventing cerebral disorders such as amnesia and dementia.

Another aspect of the present invention provides a process for the preparation of KS-505, which comprises culturing a microorganism of the genus Streptomyces and capable of producing KS-505 in a medium to accumulate KS-505 in the cultured broth, and recovering the resultant KS-505 therefrom as the free acid or a pharmaceutically acceptable salt thereof.

A further aspect of the present invention provides a pharmaceutical composition for improving the cerebral function, which comprises as an active ingredient an effective amount of KS-505 and/or a pharmaceutically acceptable salt thereof, in association with a pharmaceutically acceptable carrier or excipient.

The present invention will now be described in more detail.

I) The physicochemical characteristics of compound KS-505 of the present invention are as follows:

① Nature: White powder. Acidic substance.

② $F_{AB}$ mass spectrum: m/z 1075 (M+H—H$_2$O)$^+$[*1] and 1115 (M+Na)$^+$[*2]

③ High resolution $F_{AB}$ mass spectrum: m/z 1115.5903 [*2]

Calculated as $C_{61}H_{88}O_{17}Na$ 1115.5920.

[Notes:-*1 measured without addition of NaCl. *2 measured with addition of NaCl in conventional manner].

④ Molecular formula: $C_{61}H_{88}O_{17}$.

⑤ $^1H$ NMR spectrum:(400 MHz, 10 mg/0.4 ml CD$_3$OD).

δ (ppm); 0.77(s), 0.80(br s), 1.05(d), 1.10(s). 1.37(s), 1.52(m), 1.83(m), 2.31(m), 2.45(m), 2.79 (br t),2.94(dd), 3.34(s), 3.52(s), 3.61(br s), 3.72(m), 3.81(d), 3.90(d), 4.36(d), 7.16(d), 7.29(d)

⑥ $^{13}C$ NMR spectrum:(100 MHz, 10 mg/0.4 ml CD$_3$OD).

δ (ppm); 11.4(q), 15.0(q), 16.3(q), 17.4(q), 18.2(t), 18.7(q), 18.9(t), 20.2(t), 20.9(t), 22.0(t), 22.6(t), 23.0(q), 23.1(q), 24.5(q), 29.6(t), 34.1(t), 35.4(t), 36.7(t), 38.4(t), 39.5(s), 39.7(t), 39.8(s), 40.5(s), 42.8(s), 43.1(s), 43.3(d), 43.4(t), 44.1(t), 44.2(s), 44.4(d), 45.1(t), 50.5(s), 52.3(q), 53.9(d), 59.1(d), 60.3(t), 61.2(q), 62.7(d), 63.2(t), 64.1(d), 64.3(d), 65.1(d), 65.7(d), 73.2(d), 76.7(d), 77.0(d), 81.1(s), 84.7(d), 88.2(d), 107.3(d), 107.6(s) & 108.0(s), 122.0(d), 123.5(s), 125.4(d), 126.0(s), 142.6(s) & 142.8(s), 156.1(s), 170.2(s), 172.4(s), 174.9(s), 177.7(s).

⑦ Infrared absorption spectrum: (KBr method) 3450, 2950, 1730, 1715, 1460, 1385, 1270, 1240, 1120, 1045 cm$^{-1}$.

⑧ Ultraviolet absorption spectrum:(λ max in methanol) 221 nm(logε=4.47), 308 nm(log ε=3.63):

⑨ Specific rotation: $[α]_D^{25} = -63.5°$ (c 0.1, in methanol) measured immediately after dissolution.

⑩ Melting point: Indefinite. Gradually becomes brown.

⑪ Colour reactions: Positive in the reactions with anisaldehyde, sulfuric acid, iodine and bromocresol green. Negative in the reactions with ninhydrin, dinitrophenylhydrazine, ferric chloride and aniline-phthalic acid; Rydon-Smith's reaction and Dragendorff's reaction.

⑫ Solubility in various solvents: Soluble in methanol, dimethylsulfoxide, ethyl acetate and aqueous base. Sparingly soluble in hexane, chloroform and aqueous acid.

KS-505 is a compound consisting a γ-hydroxy-γ-lactone which can ring-open to form a compound of the following formula (II) which is chemically equivalent to KS-505. In solution, the latter is in equilibrium with KS-505, the ratio of the two forms varying depending, for example, upon the acidity of the solvent used:

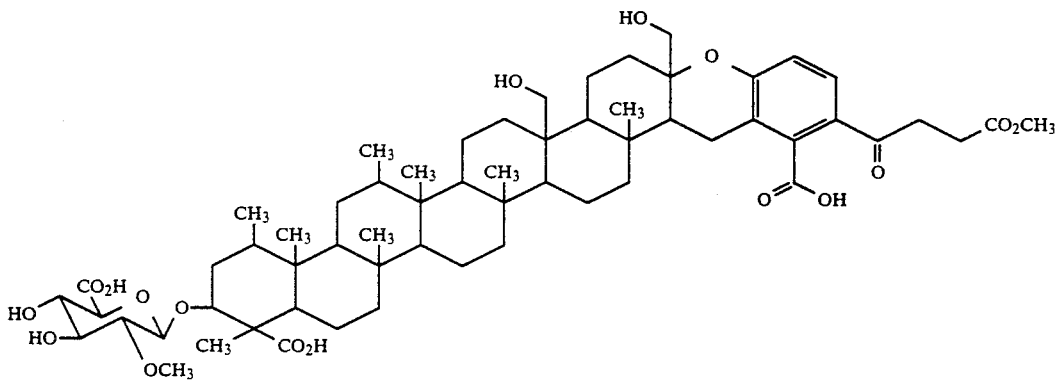

It should be understood that reference to formula (I) herein includes formula (II) and a mixture of formulae (I) and (II).

II) Salts of KS-505:

Pharmaceutically acceptable salts of KS-505 are exemplified by those formed with suitable organic or inorganic bases. Examples of suitable organic bases include primary amines such as methylamine, ethylamine and aniline; secondary amines such as dimethylamine, diethylamine, pyrrolidine, piperidine, morpholine and piperazine; and tertiary amines such as trimethylamine, triethylamine, N,N-dimethylaniline and pyridine.

Suitable inorganic bases are exemplified by alkali metals such as sodium and potassium; and alkaline earth metals such as magnesium and calcium.

These salts may be prepared in the conventional manner.

For example, sodium salt of KS-505 is represented by the following formula (III):

δ (ppm); 11.3 (q), 14.8 (q), 15.9 (q), 17.1 (q), 17.6 (t), 17.7 (t), 18.4 (q), 20.0 (t), 20.7 (t), 21.2 (t), 21.8 (t), 22.9 (q) X 2, 24.9 (q), 29.3 (t), 32.7 (t), 33.4 (t), 34.8 (t), 36.0 (t), 36.3 (t), 37.8 (s), 38.8 (s), 39.1 (s), 39.2 (t), 42.1 (s) X 2, 42.3 (t), 42.5 (s), 43.2 (d), 43.9 (d), 44.6 (t), 51.0 (s). 53.2 (q). 53.4 (d), 59.0 (d), 59.2 (t), 61.2 (q), 62.5 (d), 63.2 (d), 63.2 (t), 63.7 (d). 65.1 (d), 65.2 (d), 73.1 (d), 76.0 (d). 77.1 (d), 81.1 (s), 83.5 (d), 90.4 (d), 105.9 (d) .5 (d), 119.6 (s), 125.6 (s), 130.0 (d), 144.1 (s), 157.3 (s), 176.1 (s), 177.2 (s) X 2, 182.4 (s), 201.6 (s)

⑥ Infrared absorption spectrum: (KBr method) 3430, 2920, 1715, 1600, 1570, 1435, 1380, 1240, 1040 $cm^{-1}$.

⑦ Ultraviolet absorption spectrum: λ max (in methanol) 216 nm(logsε=4.15), 280 nm(log ε=4.01) .

⑧ Melting point: Indefinite. Gradually becomes brown.

⑨ Solubility in various solvents: Readily soluble in water, methanol and dimethyl sulfoxide.

The above-mentioned physicochemical characteristics

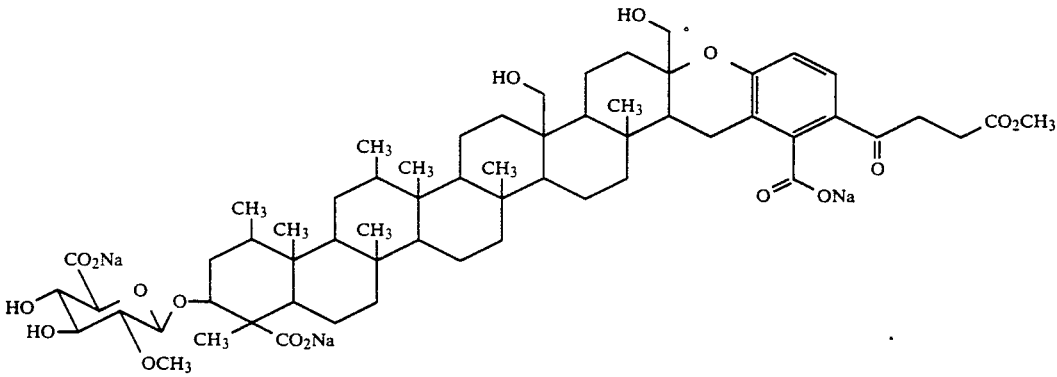

The physicochemical characteristics of the sodium salt of the formula (III) are as follows:

① Nature: White powder. Neutral substance.
② Mass spectrum (SIMS) : m/z 1115 $C_{61}H_{88}O_{17}Na)^+$.
③ Molecular formula: $C_{61}H_{85}O_{17}Na_3$.
④ $^1H$ NMR spectrum: 400 MHz, 7 mg/0.4 ml $CD_3OD$).

δ (ppm); 0.78(s), 0.81(br s), 0.97(d), 1.09(s), 1.39(s), 1.52(m), 1.85(m), 2.27(m), 2.48(m), 2.72(m), 2.94(t), 3.35(s), 3.53(s), 3.64(s), 3.73(m), 3.80(d), 3.92(d), 4.40(d), 7.05(d), 7.43(d).

⑤ $^{13}C$ NMR spectrum: (100 MHz, 20 mg/0.4 ml $D_2O$).

have been measured using the following instruments:

NMR spectrum: AM-400 (commercial product of Bruker, West Germany)

Mass spectrum: JMS-HX110 (commercial product of Nihon Denshi K.K., Japan) and M-80-B (commercial product of Hitachi Ltd., Japan)

IR absorption spectrum: IR-27G (commercial product of Shimazu Co., Japan).

UV absorption spectrum: Double beam spectrophotometer Type 200-20 (commercial product of Hitachi Ltd.,Japan)

Specific rotation: Model 141 (commercial product of Perkin-Elmer Corpn., U.S.A.)

Melting point: Micro melting-point measuring device (commercial product of Yanagimoto Seisakusho, Japan).

Table 1 indicates Rf values of KS-505 obtained by thin layer chromatography using various solvent systems, where KS-505 was detected with visualization by UV at 254 nm.

TABLE I

| Silica gel plate | Solvent system | Rf |
|---|---|---|
| 60F$_{254}$* | A | 0.23 |
| 60F$_{254}$* | B | 0.44 |
| 60F$_{254}$* | C | 0.07 |
| RP-18F$_{254}$S** | D | 0.38 |

Notes:
A chloroform/methanol/ethanol/water = 10:4:4:2
B chloroform/methanol/ethanol/water/acetic acid = 10:4:4:1:1
C chloroform/methanol/ethanol/water/conc. aqueous ammonia = 10:4:4:1:1
D 70% methanol
*Art 5628 (Merck)
**Art 13724 (Merck)
Ascending development at room temperature for 15–40 minutes.

III) Preparation of KS-505:

KS-505 may be obtained by culturing a microorganism of the genus Streptomyces capable of producing KS-505 in a medium to accumulate KS-505 in the cultured broth and recovering the resultant KS-505 therefrom.

It is preferred to use for the process of the present invention Streptomyces argenteolus A-2 (hereinafter referred to as Strain A-2) which we have isolated from the soil at a place near Shojiko, Yamanashi-ken, Japan, although any and all strains may be used so far as they belong to the genus Streptomyces and are capable of producing KS-505.

The mycological characteristics of Strain A-2 are as follows:

(1) Morphological characteristics:

Strain A-2 grows normally or abundantly on various synthetic and organic media of known types to form grey aerial mycelia. Vegetative hyphae are usually coloured light yellow. Fragmentation of mycelia is not observed. Sporangiophores are in the form of a straight chain which is simply branched from the aerial mycelia. Spores are in the form of a spiral. 10 or more spores form a chain. Grown spores are in the form of an egg or sphere and measure 0.7–0.9 μm × 1.0–1.1 μm. The spores have smooth surfaces and no flagellum.

(2) Cultural characteristics on various media:

The following Table 2 indicates the cultural characteristics obtained by culturing on various media at 28° C. In this table, the colour and tone of each culture are expressed with reference to Color Harmony Manual, 4th edition, published by Container Corp. of America, Chicago, U.S.A. (1958). The results shown herein were noted 2 weeks after the beginning of culturing.

TABLE 2

| Medium | Cultural characteristics |
|---|---|
| Glucose-asparagine agar | G: Moderate. |
| | AM: Moderate. Pearl(3ba) |
| | R: Yellow tint(1ba)-cream (1½ ca) |
| | SP: Not found. |
| Glycerol-asparagine agar | G: Moderate. |
| | AM: Moderate. Pearl(3ba) |
| | R: Cream (1½ ca) |
| | SP: Light yellow |
| Sucrose-nitrate agar | G: Moderate. |
| | AM: Moderate. Pearl(3ba) |
| | R: Ivory tint (2cb) |
| | SP: Not found |
| Starch-inorganic agar | G: Moderate. |
| | AM: Moderate. Pearl(3ba) |
| | R: Shell (3ca) |
| | SP: Not found |
| Tyrosine agar | G: Moderate. |
| | AM: Moderate. Pearl(3ba) |
| | R: Shell (3ca) |
| | SP: Not found |
| Nutrient agar | G: Moderate. |
| | AM: Abundant. Sand (3cb) |
| | R: Cream (1½ ca) - Bamboo (2gc) |
| | SP: Not found |
| Malt extract-yeast agar | G: Full. |
| | AM: Abundant. Sand (3cb) |
| | R: Clove brown (3ni)-Cinnamon (3 l e) |
| | SP: Not found |
| Oatmeal agar | G: Moderate. |
| | AM: Poor. Sand (3cb) |
| | R: Colourless |
| | SP: Not found |
| Peptone-yeast-iron agar | G: Full. |
| | AM: Poor. Natural (3dc) |
| | R: Light amber (3ic) |
| | SP: Not found |
| Hickey-Tresner's agar | G: Moderate. |
| | AM: Moderate. Pearl(3ba) |
| | R: Bamboo (2gc)-Light ivory (2ca) |
| | SP: Not found |

Notes: G ... Growth, AM ... Aerial mycelia, R ... Reverse, SP ... Soluble pigment (3) Physiological characteristics:
(a) Growth temperature (optimum)  28–35 °C.
(b) Liquefaction of gelatin:  negative
(c) Hydrolysis of starch:  positive
(d) Coagulation or peptonization of skim milk:  negative
(e) Formation of melanoid pigment  negative
(f) Assimilability of carbon sources (Bridham-Gottlieb inorganic medium viz. ISP No. 9 medium)
Assimilable: D-xylose, D-glucose, D-fructose, sucrose, L-rahmnose and D-mannitol.
Not assimilable:
L-arabinose, i-inositol and raffinose.
(g) Decomposition of cellulose:  negative
(h) Optimum pH 6.5~7.8
(i) Formation of tyrosinase  negative (4) Chemical analysis of the cell wall:

By hydrolysis of the whole cells, it has been observed that the cell walls contain LL-diaminopimelic acid.

For example, with reference to the characteristics of the spore chain on the aerial mycelia and to the type of diaminopimelic acid, the present strain may be classified into the genus Streptomyces. By reference to various characteristics such as, for example, ① greyish aerial mycelia,
② spiral spores,
③ smooth surfaces of the spores,
④ lack of formation of melanoid pigment,
⑤ either the lack of formation of soluble pigment or the lack of formation of light yellowish soluble pigment and
⑥ assimilability of carbon sources, as well as by reference to various known microorganisms, which have been reported and recognized by The American Society of Bacteriology [see, for example, Int. J. Syst. Bacteriol. 30, 225 (1980)], the present strain is believed to be identical with Streptomyces argenteolus with the exception that the latter does not assimilate sucrose, but L-arabinose. Accordingly, the present strain has been designated by us as Streptomyces argenteolus A-2.

This strain has been deposited with Bikoken (The Fermentation Research Institute of Industrial Science and Technology) located at 1-3, Higashi 1-chome, Tsukuba-shi, Ibaraki-ken, Japan on 21 September 1988 as FERM BP-2065 under the protocol of the Budapest Treaty.

Microorganisms which may be used for the process of the present invention may be cultured in the conventional manner applicable to various microorganisms of the genus Streptomyces using synthetic or organic media containing suitable amounts of assimilable sources of carbon, nitrogen and organic substances.

Examples of carbon sources which may be used for this purpose include various carbohydrates such as glucose, fructose, sucrose, lactose, starch, dextrin, mannose, maltose, molasses and mushed potato; organic acids such as citric acid, acetic acid and fumaric acid; alcohols such as methanol and ethanol; hydrocarbons such as methane, ethane and n-propane; amino acids such as glutamine; glycerol and cotton seed oil, any of which may be used alone or in combination.

Examples of suitable nitrogen sources include ammonium chloride, ammonium sulfate, ammonium nitrate, ammonium phosphate and other ammonium salts; amino acids such as aspartic acid, glutamic acid, cystine and alanine; urea, malt extract, meat extract, yeast extract, dry yeast, corn steep liquor, soybean powder, cotton seed oil, Casamino acid, Pharmamedia (commercial product of Proctor & Gamble, U.S.A.), soluble vegetable protein, vegetable juice and fruit juice, each of which may be used alone or in combination.

Examples of suitable inorganic substances include potassium dihydrogen phosphate, sodium dihydrogen phosphate, magnesium phosphate, magnesium sulfate, ferrous sulfate, manganese sulfate, cobalt sulfate, zinc sulfate, ammonium molybdate, potassium aluminium sulfate, barium carbonate, calcium carbonate, cobalt chloride, magnesium chloride, potassium chloride and sodium chloride, which may be used alone or in combination.

If desired, the medium may further contain, for example, vitamins such as panthothenic acid and buffers such as 3-(N-morpholino)propanesulfonic acid in order to promote or stabilize the growth of the microorganism, or the production of KS-505. In the case where the microorganism used requires a special substance for growth, it is possible to add such a substance to the medium.

It is preferred to culture the microorganism with shaking or stirring. Especially good results may be obtained by culturing with stirring and aeration. Culturing may usually be effected at a temperature of from 20°–40° C., preferably from 25° to 30° C. and at a pH of from about 6 to 8. Culturing may usually be continued for a period of from 3 to 10 days to accumulate a large amount of KS-505 in the cultured liquor and the cells.

After completion of fermentation, KS-505 may be recovered and purified by conventional techniques, for example, by extraction of KS-505 from the cells with suitable solvents such as ethanol and acetone; removal of the cells by filtration or centrifugation; distribution using a suitable solvent system such as column chromatography or thin layer chromatography using absorption resin silica gel, silanized silicate, alumina, cellulose, diatomaceous earth or gel filtration agents. In this manner, it is possible to isolate KS-505.

In one preferred embodiment, KS-505 may be recovered and purified as from the cultured broth as follows:

The cultured broth is filtered or centrifuged to remove the cells. The resultant filtrate or supernatant is passed through a column packed with an adsorption resin, for example, Diaion HP-20 (commercial product of Mitsubishi Kasei Corp. K.K., Japan) to adsorb the active material, followed by elution using a suitable solvent (for example, methanol). The elate is concentrated under reduced pressure and dissolved in a suitable solvent, for example, a mixture of chloroform/methanol/ethanol/water (10:4:4:1 v/v).

The solution is then subjected to silica gel column chromatography using a solvent system having the same composition; if desired, the chromatographic treatment may be repeated twice or more times using a suitable solvent system. Active fractions are collected, combined and concentrated under reduced pressure.

From the concentrated solution, KS-505 may be extracted acidic conditions using a suitable solvent which is not miscible with water (for example, ethyl acetate). The extracted solution is concentrated and subjected to silica gel column chromatography using a solvent system in a similar manner to that described above. If desired, chromatographic treatment may be repeated. The fractions containing crude KS-505 are collected, combined and dissolved in a suitable acidic solvent such as, for example, a mixture of methanol/water/acetic acid and is then subjected to preparative high performance liquid chromatography using a mixture of methanol/ammonium acetate buffered solution (7:3 v/v) to obtain KS-505 in the form of a white powder.

In the purification step, KS-505 may be detected by thin layer chromatography using a fluorescein-stained silica gel plate, followed by visualization with UV at 254 nm.

IV) Pharmaceutical composition:

The pharmaceutical composition according to the present invention comprises an effective amount of compound KS-505 or a pharmaceutically acceptable salt thereof in association with a pharmaceutically acceptable carrier or excipient. Owing to the anti-amnesia activity of KS-505, the pharmaceutical compositions may be used for curing and preventing disorders of cerebral function such as amnesia and dementia.

Preferred dosage rates of the composition will vary, depending upon various factors such as, for example, the desired effects, the method and period of administration, the age and body weight of the patients, but for general guidance, it is suggested that usually 0.01–100 mg/kg calculated as KS-505 may be used for adult patients through the oral route or parenteral route (for example, by injection, intraveneous drip infusion, rectal administration using suppositories, percutaneous ointment etc.).

KS-505 is well tolerated, the Na salt was not lethal to ddy male mice at 1000 mg/kg per os. On intraperitioneal administration, an $LD_{50}$ value of 417.5 mg/kg was observed.

Although it is possible to administer KS-505 per se, usually KS-505 may be formulated, for example, in the forms of tablets, pills, powders, granules, capsules, suppositories, injection agents and drip infusion agents. Various methods for such formulation are well known in the art.

The pharmaceutical composition of the present invention may comprise, for example, various excipients, lubricants, binders, disintegrators, dispersants, isotonizating agents, emulsifiers and absorption-enhancing agents.

Examples of carriers which are suitable for this purpose include water, distilled water for injection, physiological saline, glucose, fructose, white sugar, mannitol, lactose, starch, corn starch, cellulose, methylcellulose, carboxymethylcellulose, hydroxypropyl cellulose, arginic acid, talc, sodium citrate, calcium carbonate, monobasic calcium phosphate, magnesium stearate, urea, silicone resin, sorbitan fatty acid ester and glycerol fatty acid ester.

The pharmaceutical composition may, for example, contain KS-505 in an amount of 0.01-85% by weight.

The following non-limiting examples and experiment illustrate the present invention.

EXAMPLE 1

*Streptomyces argenteolus* A-2 (FERM BP-2065) was used as the seed. A medium containing glucose (1.0 g/dl), soluble starch (1.0 g/dl), meat extract (0.3 g/dl; commercial product of Kyokuto Pharmaceutical Industries, Japan), yeast extract (0.5 g/dl; commercial product of Daigo Eiyou Kagaku K.K., Japan), peptone (0.5 g/dl; commercial product of Difco., U.S.A.) and calcium carbonate (0.2 g/dl) and having a pH of 7.2 was used as the seed medium.

The seed strain was transferred to the seed medium (10 ml) put in a test tube for culturing with shaking at a temperature of 28° C. for 5 days. The seed culture (4 ml) was inoculated into a seed medium (40 ml) having the same composition and put in an Erlenmeyer flask (300 ml) for culturing with shaking at a temperature of 28° C. for 2 days. The resultant seed culture (1.8 l) was innoculated into a fermentation medium (18 l) put in a 30 l jar fermentor, the fermentation medium having the following composition:

glucose (1.0 g/dl), maltose (4g/dl), 3-(N-morpholino)-propanesulfonic acid (1.0 g/dl), magnesium sulfate.$7H_2O$ (0.05 g/dl), soybean powder (1.5 g/dl), Pharmamedia (1.5 g/dl, Procter & Gamble. U.S.A) and calcium carbonate (0.5 g/dl) [pH 7.0].

Culturing was effect with stirring (300 r.p.m.) and aeration (18 l/min.) at a temperature of 28° C. for 5 days. After completion of culturing, the culture was centrifuged (7000 r.p.m.) to collect the supernatant. The supernatant was passed through a column (2 l) packed with Diaion HP-20 (commercial product of Mitsubishi Kasei Kogyo K.K., Japan) and washed in turn with 6 l of water, 6 l of 50% methanol and 10 l of methanol. Then elution was effected using methanol containing 1% ammonia (10 l). The fractions of methanol containing 1% ammonia were collected, combined and concentrated under reduced pressure to obtain a brown oil (about 2.7 g) which was dissolved in a mixture (10 ml) of chloroform/methanol/ethanol/water (10:4:4:1 v/v). The solution was applied to the top portion of a silica gel column (500 ml; packed with Wako gel C-200 [Wako gel is a commercial product of Wako Pure Chemical Industries, Ltd., Japan] filled with a mixture having the same composition as mentioned above). Development was effected using a solvent system having the same composition as mentioned above (1500 ml) and methanol (1000 ml) in this order.

The eluate was then collected and concentrated under reduced pressure to obtain an oil (1.5 g) which was dissolved in a mixture of chloroform/methanol/ethanol/water (4 ml, 10:4:4:1 v/v), which was then applied to the top portion of a silica gel column (200 ml; packed with Wako gel C-200 and filled with a mixture having the same composition as mentioned above. The eluate was collected and divided into small fractions (each 10 ml). Active fraction Nos. 17–42 were combined and concentrated under reduced pressure to obtain a brown oil (about 460 mg). The oil was then suspended in about 50 ml of 10% methanol and adjusted to pH 2 with 2N hydrochloric acid.

Extraction was effected with three 400 ml portions of ethyl acetate. The ethyl acetate layers were collected, combined and concentrated under reduced pressure to obtain a brown solid (266 mg).

This material was dissolved in a mixture of chloroform/methanol/ethanol/water (1 ml; 10:4:4:1 v/v) and applied to the top portion of a silica gel column (50 ml; packed with Wako gel C-300 and filled with a mixture having the same composition). Development was effected using a solvent system having the same composition as mentioned above. The eluate was collected and divided into small fractions (each 5 ml).

The active fraction Nos. 13–25 were collected, combined and concentrated under reduced pressure to obtain a light brownish solid material (about 256 mg) which was then dissolved in a mixture (1 ml) of chloroform/methanol/ethanol/water (10:4:4:1 v/v). This solution was applied to a Lobar column (Lichroprep Si60, Size B, commercial product of Merck AG., West Germany) which had been equilibrated with a mixture having the same composition as mentioned above.

A solvent system (1000 ml) having the same composition as mentioned above was used for development. Development was further effected using a mixture (900 ml) of chloroform/methanol/ethanol/water (10:4:4:2 v/v). The eluate was divided into small fractions (each 10 ml). Active fraction Nos. 14–34 were collected, combined and concentrated under reduced pressure to obtain a light brown powder (56 mg).

The powder was dissolved in a similar mixture of methanol/water/acetic acid (28 ml). The solution was subjected several times to preparative high performance liquid chromatography under the following conditions:

Instrument . . . LC6A System (commercial product of Shimazu Co., Japan)

Column . . . Radial-Pak TM (8$\phi$×100 mm) filled with Nova-Pak (ODS, 4 $\mu$m) (commercial products of Waters, U.S.A.)

Eluant . . . Methanol/0.2M ammonium acetate buffered solution (pH 7.0) (7:3 v/v)

Sample volume . . . 1 mg once

Eluting rate . . . 3.0 ml/min.

The fractions having the retention time of 3.0–4.3 minutes were collected, combined and concentrated under reduced pressure. The concentrated material was freeze-dried to obtain a white powder (40 mg) which was then dissolved in 1N hydrochloric acid (20 ml). The solution was extracted 3 times with 60 ml portions of ethyl acetate. The organic layers were collected, combined, washed with saturated solution of sodium chloride and dried over magnesium sulfate. The solvent was evaporated reduced pressure. There was obtained KS-505 (33 mg) in the form of white powder.

During the purification step, KS-505 was detected by thin-layer chromatography using a fluorescein-stained silica gel plate (60$F_{254}$ plate; Art 5715, commercial product of Merck AG.) developed by a solvent system of chloroform/methanol/ethanol/water (10:4:4:2 v/v), followed by visualization under UV at 254 nm.

EXAMPLE 2

KS-505 (96 mg; obtained by the method of Example 1) and sodium bicarbonate (22 mg) were dissolved in water (15 ml). The solution was freeze-dried to obtain sodium salt of KS-505 (101 mg).

EXAMPLE 3

Tablet:

To a mixture of KS-505 (100 g), lactose (35 g), corn starch (18 g) and carboxymethylcellulose calcium (10 g) was added 10% solution of hydroxypropyl cellulose (50 g). After well kneading, the material was treated in a tabletting machine equipped with a screen with 0.1 mm openings. To the resultant material was added magnesium stearate (2 g) and the mixture was processed in conventional manner to obtain tablets, each of which (170 mg; diameter 8 mm) contained 100 mg of KS-505.

EXAMPLE 4

Capsule:

To a mixture of KS-505 (50 g), lactose (75 g) and potato starch (38 g) was added 10% solution of hydroxypropyl cellulose (50 g). The material was well kneaded and granulated in a similar manner to that described in Example 3. After adding magnesium stearate (2 g), the material was put into capsules in conventional manner to prepare the desired capsules (each 170 mg) containing 50 mg of KS-505.

EXAMPLE 5

Soft capsule:

KS-505 (10 g) was added to 100 g of soybean oil. The resultant solution was put into capsules in conventional manner to prepare the desired soft capsules (each 110 mg) containing 10 mg of KS-505.

EXPERIMENT

The anti-amnesia activity of compound KS-505 was effected in a conventional manner as follows:

As test animals, male mice (ddy strain; body weight 24–28 g; each group consisting of 15 mice) were used. With reference to the passive avoiding action of Step-through Type 1 of the animals, influence of KS-505 upon the learning efficiency of the animals was tested in the following manner:

A dark adaptometer, comprising a light room (15×9×11 cm; illuminated with a 4 W white fluorescent lamp) and a dark room (15×14×18 cm), was used for the experiment. Between the two rooms, a guillotine door (3×3 cm) was provided as a partition. Each room had a grid floor made of stainless steel. In the dark room, it was possible to supply a weak electric current to the animal from the floor.

On each occasion, physiological solution of sodium chloride (20 µl) containing 5, 20 or 50 µg of KS-505 (sodium salt) was used as the test sample, and a physiological solution of sodium chloride containing no KS-505 sodium salt was used as the control.

A test solution (20 µl) was administered into the left ventricule of the test animal using a two-step needle. 30 minutes after this, an acquisition test was carried out as follows:

The animal was put into the light room. Ten seconds after this, the door was opened. Immediately after the animal completely entered into the dark room, an electric current was supplied from the grid floor of the dark room to exert a foot shock (0.18 mA for two seconds, 2000 V) to the animal. Immediately after this, the animal was taken out from the dark room.

Animals requiring a time of more than 60 seconds to enter into the dark room were excluded from the subsequent treatment.

Immediately after the acquisition test, the animal was made amnesic by exerting an electric shock (25 mA, $2.5 \times 10^{-3}$ seconds, 2000 V). 24 hours after this, the the animal was again put into the light room. 10 seconds after this, the door was opened. A latency viz. an interval between the time the door was opened and the time the animal completely entered the dark room was measured. The measurement was effected for a period of 600 seconds. An interval longer than 600 seconds was calculated as 600 seconds.

As is apparent from the following Table 3, in the case where sodium salt of KS-505 was administered to the animal in an amount of 5 µg per animal, a significant anti-amnesia activity was observed. In this table, Group I indicates untreated animals, viz. animals which were not administered with sodium salt of KS-505 and which were not subjected to the amnesic treatment (electric shock). The animals of Group II were subjected to the amnesic treatment without prior administration of the sodium salt. All of the animals of Groups III to V were administered with sodium salt of KS-505 before the amnesic treatment. The amounts of the sodium salt of KS-505 administered are shown in the table.

TABLE 3

| Group | Dose | Latency (seconds)[*1] |
|---|---|---|
| Control groups | | |
| I | 20 µλ | 414.5 ± 40.1 |
| II | 20 µλ | 83.4 ± 20.4[*2] |
| Test groups | | |
| III | 5 µg | 210.7 ± 42.9[*3] |
| IV | 10 µg | 111.2 ± 21.3 |
| V | 50 µg | 125. ± 37.8 |

Notes: [*1] average ± standard error.
[*2] comparison with Group I, $p < 0.0001$
[*3] comparison with Group II, $p < 0.02$

We claim:

1. Compound KS-505 represented by the formula (I):

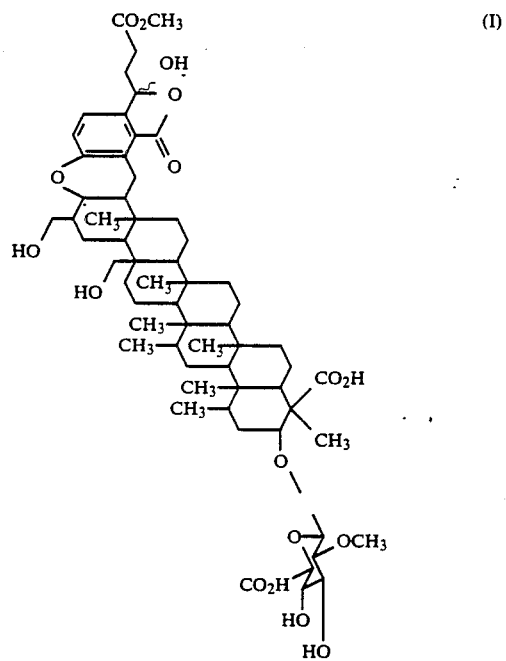

or a pharmaceutically acceptable salt thereof.

2. The compound of claim 1, wherein the salt is formed with one member selected from the group consisting of methylamine, ethylamine, aniline, dimethylamine, diethylamine, pyrrolidine, piperidine, morpholine, piperazine, trimethylamine, triethylamine, N,N-dimethylaniline, sodium, potassium, magnesium and calcium.

3. The compound of claim 2, represented by the following formula (III):

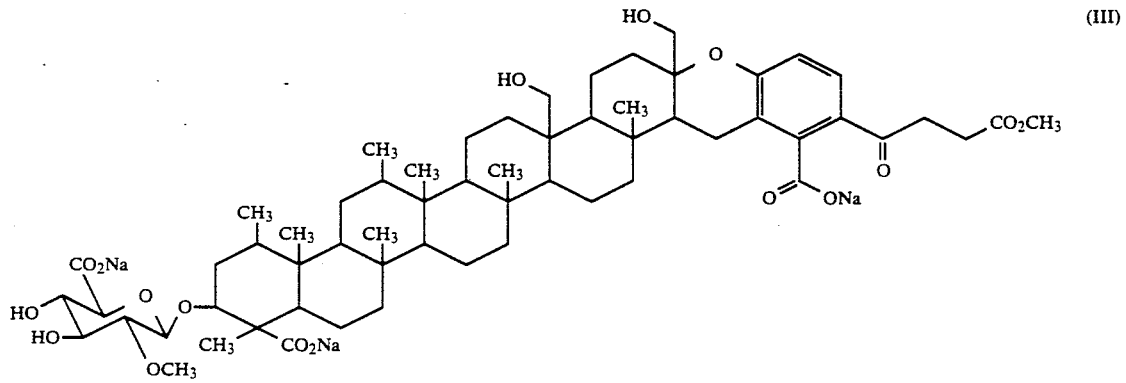

(III)

4. A pharmaceutical composition for improving the cerebral function, which comprises an effective amount of compound KS-505 or a pharmaceutically acceptable salt thereof as claimed in claim 1 in association with a pharmaceutically acceptable carrier or excipient.

5. A pharmaceutical composition of claim 4, wherein the salt is formed with one member selected from the group consisting of methylamine, ethylamine, aniline, dimethylamine, diethylamine, pyrrolidine, piperidine, morpholine, piperazine, trimethylamine, triethylamine, N,N-dimethylaniline, sodium, potassium, magnesium and calcium.

6. A compound produced by fermentation of *Streptomyces argenteolus* A-2 (FERM BP-2065), said compound having the following physicochemical properties in free acid form:

1) Nature: White powder, acidic substance;
2) $F_{AB}$ mass spectrum: m/z 1075 $(M+H-H_2O)^+$, measured without addition of sodium chloride and 1115 $(M+Na)^+$, measured with addition of sodium chloride;
3) High resolution $F_{AB}$ mass spectrum: m/z 1115.5903, measured with addition of sodium chloride, calculated as $C_{61}H_{88}O_{17}Na$: 1115.5920;
4) Molecular formula: $C_{61}H_{88}O_{17}$;
5) $^1H$ NMR spectrum: (400 MHz, 10 mg/0.4 ml $CD_3OD$)
   δ(ppm); 0.77(s), 0.80(br s), 1.05(d), 1.10(s), 1.37(s), 1.52(m), 1.83(m), 2.31(m), 2.45(m), 2.79 (br t), 2.94(dd), 3.34(s), 3.52(s), 3.61(br s), 3.72(m), 3.81(d), 3.90(d), 4.36(d), 7.16(d), 7.29(d);
6) $^{13}C$ NMR spectrum:(100 MHz, 10 mg/0.4 ml $CD_3OD$)
   δ(ppm); 11.4(q), 15.0(q), 16.3(q), 17.4(q), 18.2(t), 18.7(q), 18.9(t), 20.2(t), 20.9(t), 22.0(t), 22.6(t), 23.0(q), 23.1(q), 24.5(q), 29.6(t), 34.1(t), 35.4(t), 36.7(t), 38.4(t), 39.5(s), 39.7(t), 39.8(s), 40.5(s), 42.8(s), 43.1(s), 43.3(d), 43.4(t), 44,1(t), 44.2(s), 44.4(d), 45.1(t), 50.5(s), 52.3(q), 53.9(d), 59.1(d), 60.3(t), 61.2(q), 62.7(d), 63.2(t), 64.1(d), 64.3(d), 65.1(d), 65.7(d), 73.2(d), 76.7(d), 77.0(d), 81.1(s), 84.7(d), 88.2(d), 107.3(d), 107.6(s) & 108.0(s), 122.0(d), 123.5(s), 125.4(d), 126.0(s), 142.6(s) & 142.8(s), 156.1(s), 170.2(s), 172.4(s), 174.9(s), 177.7(s);
7) Infrared absorption spectrum: (KBr method) 3450, 2950, 1730, 1715, 1460, 1385, 1270, 1240, 1120, 1045 $cm^{-1}$;
8) Ultraviolet absorption spectrum: (λ max in methanol):
   221 nm($log_\epsilon=4.47$), 308 nm($log_\epsilon=3.63$);
9) Specific rotation: $[\alpha]_D^{25}=-63.5°$ (c 0.1, in methanol) measured immediately after dissolution;
10) Melting point: Indefinite, gradually becomes brown;
11) Colour reactions: Positive in the reactions with anisaldehyde, sulfuric acid, iodine and bromocresol green, negative in the reactions with ninhydrin, dinitrophenylhydrazine, ferric chloride, and anilinephtalic acid; Rydon-Smith's reaction and Dragendorff's reaction;
12) Solubility in various solvents: Soluble in methanol, dimethylsulfoxide, ethyl acetate and aqueous base; sparingly soluble in hexane, chloroform and aqueous acid or a pharmaceutically acceptable salt thereof.

* * * * *

UNITED STATES PATENT AND TRADEMARK OFFICE
CERTIFICATE OF CORRECTION

PATENT NO. : 5,079,232

DATED : January 7, 1992

INVENTOR(S) : Keiko Ohsawa, et al

It is certified that error appears in the above-identified patent and that said Letters Patent is hereby corrected as shown below:

On the title page, item [73] Assignee, should be changed to read as follows:

--[73] Assignee: Kyowa Hakko Kogyo Kabushiki Kaisha, Japan--.

Signed and Sealed this

Thirteenth Day of April, 1993

Attest:

STEPHEN G. KUNIN

*Attesting Officer*  *Acting Commissioner of Patents and Trademarks*